United States Patent [19]
Reynolds

[11] Patent Number: 5,370,610
[45] Date of Patent: Dec. 6, 1994

[54] SURGICAL DRAINAGE TUBE SYSTEM

[76] Inventor: James R. Reynolds, 1100 S. Euclid Ave., Sioux Falls, S. Dak. 57105

[21] Appl. No.: 15,649

[22] Filed: Feb. 9, 1993

[51] Int. Cl.$^5$ .............................................. A61M 3/00
[52] U.S. Cl. ...................................... 604/43; 604/93; 604/280
[58] Field of Search ............... 604/264, 280, 284, 43, 604/45, 93

[56] References Cited

U.S. PATENT DOCUMENTS

| | | |
|---|---|---|
| 545,102 | 8/1895 | Sleem . |
| 1,131,349 | 3/1915 | Ellis . |
| 1,191,736 | 7/1916 | Roberson . |
| 1,215,512 | 2/1917 | Fetzer . |
| 1,740,174 | 12/1929 | Hevern . |
| 2,560,915 | 7/1951 | Bamberger . |
| 2,667,682 | 2/1954 | Stone . |
| 2,930,378 | 3/1960 | Buyers . |
| 3,421,510 | 1/1969 | Kettenbach . |
| 3,675,639 | 7/1972 | Cimber . |
| 3,810,471 | 5/1974 | Truhan . |
| 4,274,417 | 6/1981 | Delpy ........................ 604/280 X |
| 4,382,442 | 5/1983 | Jones . |

(List continued on next page.)

OTHER PUBLICATIONS

D. J. Abramson, "Improved Triple Lumen all Purpose Drains and Their Care and Management", in *The American Surgeon*, vol. 49, No. 10, pp. 539-541, (Oct. 1983).

(List continued on next page.)

*Primary Examiner*—Gene Mancene
*Assistant Examiner*—Thomas Price
*Attorney, Agent, or Firm*—Fredrikson & Byron

[57] ABSTRACT

A multi-lumen drainage tube or catheter body includes a primary drainage lumen and separate auxiliary lumens with obstructed proximal ends wherein the tube may be used a simple, single lumen drainage tube, a two lumen drainage tube or a three lumen drainage tube by removal of one or both of the obstructions from the proximal ends of the auxiliary lumens and connection of the lumen openings at the proximal end of the drainage tube to the corresponding single or multi-lumen adaptor. In the second aspect of the invention, a drainage tube system is provided which may employ the adaptable multi-lumen drainage tube of the first aspect of the invention and wherein the adaptors employed therewith are provided with a mechanism for selectively inserting a flexible, elongated clean-out catheter into and down the length within the main drainage lumen to pass the distal end of the catheter through accumulated matter and to introduce a high suction pressure through the clean-out catheter lumen to evacuate the loosened obstructing matter from the main drainage lumen. The adaptor through which the clean-out catheter is introduced preferably includes a main lumen connector adapted to be connected to the drainage lumen and having two branches extending therefrom. The main branch preferably includes a valve for closing the first branch and a further connector for connection of the main drain lumen to the fluid collection vessel and low pressure pump when the valve is opened. The second branch preferably includes a connector having a fluid seal therein that bears against the exterior surface of the clean-out catheter and through which the clean-out catheter may be advanced and retracted. The clean-out catheter is preferably encased within a flexible, compressible sheath wherein both the sheath and the proximal end of the clean-out catheter are joined at a normally-closed valve and connector body adapted to be connected to a high suction pressure source and collection vessel.

11 Claims, 4 Drawing Sheets

U.S. PATENT DOCUMENTS

| | | | |
|---|---|---|---|
| 4,508,533 | 4/1985 | Abramson | 604/45 X |
| 4,573,965 | 3/1986 | Russo . | |
| 4,693,257 | 9/1987 | Markham | 604/44 X |
| 4,723,955 | 2/1988 | Vaillancourt . | |
| 4,735,606 | 4/1988 | Davison . | |
| 4,744,364 | 5/1988 | Kensey . | |
| 4,796,637 | 1/1989 | Mascuch et al. | 604/280 X |
| 4,852,568 | 8/1989 | Kensey . | |
| 4,917,667 | 4/1990 | Jackson | 604/264 X |
| 5,029,580 | 7/1991 | Radford et al. | 604/43 X |
| 5,073,164 | 12/1991 | Hollister et al. . | |
| 5,108,364 | 4/1992 | Takezawa et al. | 604/43 |

OTHER PUBLICATIONS

A. L. Vercoutere, M.D., et al, "Improved Method For Intra-Abdominal Drainage", in *Surgery, Gynecology & Obstetrics*, vol. 158, pp. 587–588, (Jun. 1984).

J. P. A. M. Vroemen, M.D., et al, "A Simple Procedure For Relieving Obstruction of Sump Catheters", in *The Surgeon At Work*, vol. 165, pp. 267–268, (Sep. 1987).

R. F. Edlich, M.D., Ph.D., et al, "Evaluation of a New, Improved Surgical Drainage System", in *The American Journal of Surgery*, vol. 149, pp. 295–298, (Feb. 1985).

R. L. Beaudet, M.D., "New Technique For Drainage After Cardiac Surgery", in *The Journal of Thoracic and Cardiovascular Surgery*, vol. 78, No. 1, pp. 119–122, (Jul. 1979).

M.D. Spengler, B. S., et al, "Performance of Filtered Sump Wound Drainage Tubes", in *Surgery, Gynecology & Obstetrics*, vol. 154, pp. 333–336, (Mar. 1982).

S. Gianelli, Jr., M.D., et al, "Irrigated Sump Tube Drainage Following Open-Heart Surgery", in *Journal of the American Medical Association (JAMA)*, vol. 213, No. 6, p. 1038, (Aug. 1970).

D. E. Tribble, M.D., "An Improved Sump Drain-Irrigation Device of Simple Construction", in *Archives of Surgery*, vol. 105, pp. 511–513, (Sep. 1972).

G. T. Golden, M.D., et al, "A New Filtered Sump Tube for Wound Drainage", in *The American Journal of Surgery*, vol. 129, pp. 716–717, (Jun. 1975).

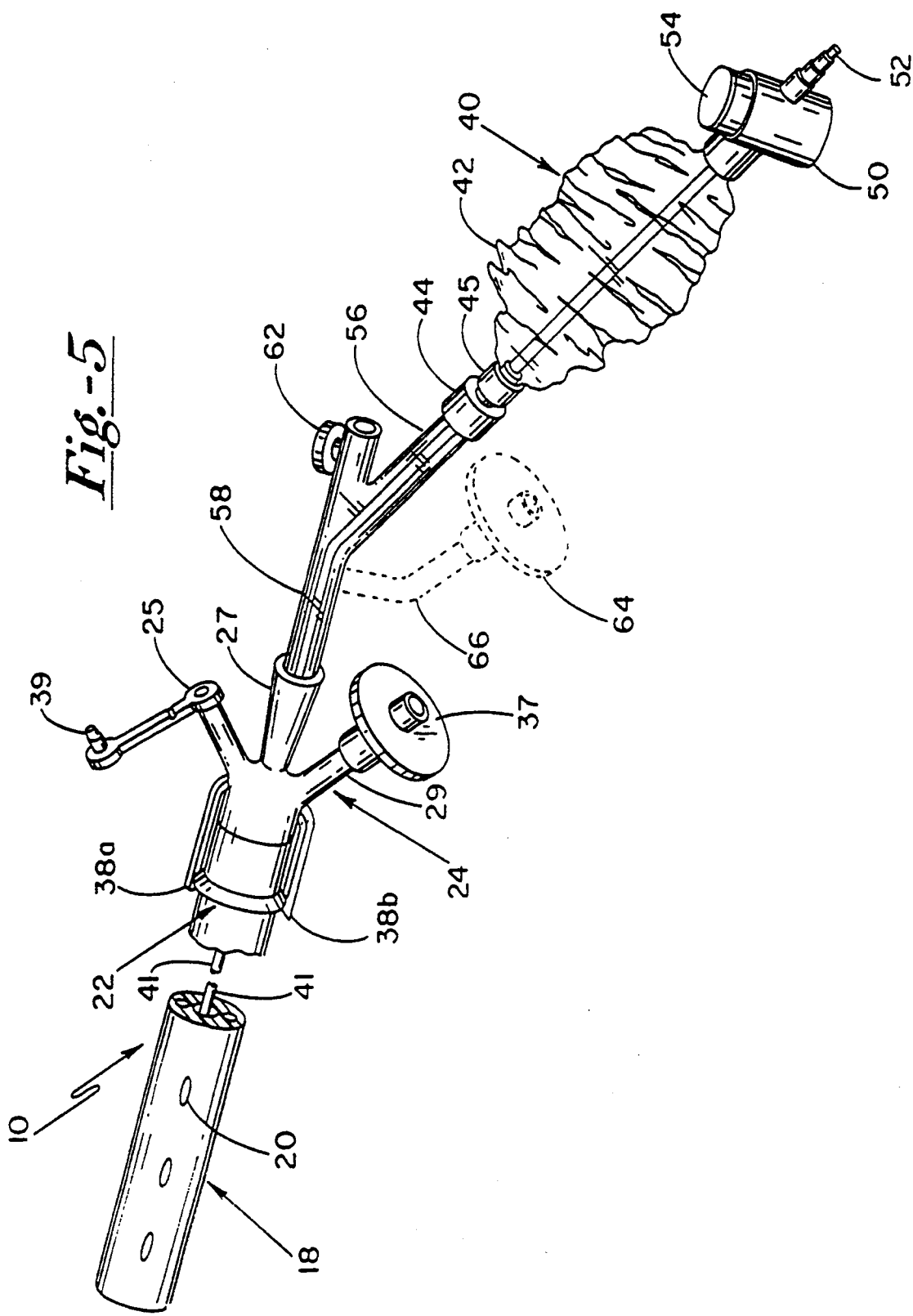

SURGICAL DRAINAGE TUBE SYSTEM

BACKGROUND OF THE INVENTION

1. Field of the Invention

The present invention relates to medical devices, and more particularly to a drainage tube system and components thereof for draining body fluids from body cavities.

2. General Background and Prior Art

During surgical procedures and following completion of surgery, drainage tubes are employed to suction body fluids from the surgical field or from within the closed wound. Following a thoracotomy, for example, drainage tubes having one or more lumens extending between the proximal and distal ends thereof are positioned with the distal end located within the chest and the body of the tube passing through the closed incision or a separate, small incision so that fluids accumulating normally postoperatively in the chest, for example, drain and flow by gravity and internal pressure to a suitable collection vessel. Suction may be applied to the drainage lumen at the proximal end of the tube to encourage the flow of body fluid. The removal of such fluids, including blood, pus, cells, blood clots, other fluids and tissue fragments ("body fluids") following surgery is beneficial to relieve pressure and avoid and/or control infections. Generally such drainage systems are referred to as "wound" drainage systems, whether or not surgery was precipitated by trauma.

To this end, a number of wound drainage systems of the type which include catheter or tube members which can be so installed such that they extend to the collection vessel have been heretofore made available. Systems of this general type have included simple, single lumen, tubes employing gravity, internal pressure or suction as described above, double lumen tubes and triple lumen tubes. The second lumen of double lumen tubes may be employed to introduce irrigating fluids into the body cavity being drained to dilute and encourage the flow of body fluids or may be used with an appropriate anti-bacterial filter at the proximal end of the second lumen to ventilate the body cavity to also encourage the flow of body fluids through the first lumen.

Triple lumen drainage tubes or catheters of the type disclosed in U.S. Pat. No. 4,508,533 to Abramson and described in the article by D. J. Abramson, "Improved Triple Lumen All Purpose Drains and their Care and Management", in *THE AMERICAN SURGEON*, vol. 49, no. 10, pp. 539-541, (October, 1983), both incorporated herein by reference, provide separate irrigation and ventilation lumens with an appropriate, removable, three lumen adaptor having appropriate valves, caps and anti-bacterial filter. During periods when the irrigation lumen is not used for irrigating the cavity, it is blocked off or otherwise closed to prevent unfiltered air, which may contain bacteria, from entering the body cavity through it.

The surgical insertion of such drainage tubes or catheters is usually made before the incision is closed through a stab wound made at a distance from the surgical incision so that the healing of the usually larger incision may proceed without complications arising from mechanical movement of the tube and possible contamination of the incision. A subcutaneous tunnel is created to the cavity to be drained, and the tube is introduced through the incision so that its proximal end is advanced through the tunnel and emerges from the stab wound. The distal end is placed in the cavity to be drained, following the precautions on placement described in the above-incorporated Abramson article. Drainage tubes or catheters with integrally formed, multi-branch connectors for drainage, irrigation, and/or ventilation are inconvenient or impossible to pull through a subcutaneous tunnel and reasonably sized stab wound. Introducing the tube or catheter distal end first requires tunneling a forceps to the stab wound and is not favored.

Depending on the nature of the procedure, surgeons find that in certain situations the simple single lumen drainage tube is sufficient. In other procedures, it may be desirable to employ the double or triple lumen tube coupled to appropriate irrigation or ventilation systems. A need exists for an adaptable multi-lumen drainage tube that may be employed in applications calling for a single lumen or two or more lumens and that may be easily introduced surgically in the manner described above and coupled securely with suitable adaptors at its proximal end.

While devices of the above-described type have frequently been used for draining, ventilating and irrigating wounds, they have not always been entirely effective for several reasons. The body fluid leaving the body cavity through the drainage lumen contains a large percentage of blood which can form clots in the lumen or at the distal end thereof resulting in stoppage. Consequently, medical personnel attending the patient must frequently check the patency of the lumen so that the drainage system remains operating effectively.

The application of suction to the drainage lumen to encourage drainage is not always effective even when irrigation and/or ventilation of the body cavity is provided. Relatively low suction pressure is necessary to avoid creating or exacerbating a negative pressure within the body cavity which, in the case of the thoracic cavity could effect lung pressure. Conversely, a positive flow of air or irrigation fluid into the lung cavity to encourage drainage could introduce a positive pressure that could lead to deflation or collapse of the lungs. In other applications, high positive and negative pressure may adversely influence body organs or cause discomfort to the patient.

Current techniques for cleaning out areas within the drainage tube containing occluding body tissue and blood clots include periodically increasing the applied suction pressure or the applied irrigation pressure. In addition, it has been proposed in a system employing a medical underwater seal collection vessel to provide a venting valve coupled to the venting lumen and periodically closing the valve to increase negative pressure inside the cavity and to suddenly open the valve so that the incoming air effectively increases the pressure and hopefully dislodges the occluding matter as disclosed in U.S. Pat. No. 4,735,606 to Davison. In the U.S. Pat. No. '606 patent, it is also proposed to manually strip the drain tube by hand squeezing the tube lumen in order to obtain momentary high negative pressures in the distal portion of the lumen in the cavity.

In coaxial, double lumen sump catheters, a further manual cleaning technique for cleaning obstructions from the inner suction lumen has been proposed in the article by J. P. A. M. Vroemen, "A Simple Procedure for Relieving Obstruction of Sump Catheters", cite needed. This technique involves slitting the outer lumen proximal to the percutaneous entry and manually snagging the inner lumen and retracting it proximally to pull it through the slit. The exposed distal length of the inner lumen is manually cleaned and reintroduced through the slit and advanced distally. The slit is then taped closed. This technique poses the risk of contamination and weakens the catheter. It cannot be used in side-by-side lumen catheters, e.g. the Abramson triple lumen catheter described above.

In spite of these improvements, a need remains for an effective and easily manipulative apparatus for removing clots and body tissue from drainage lumens in such drainage catheter systems.

SUMMARY OF THE INVENTION

It is therefore an object of the present invention to provide an improved wound drainage system wherein an adaptable wound drainage tube is employed with appropriate adaptors as a single lumen or a multi-lumen drainage system.

It is a further object of the present invention to provide an apparatus for cleaning out obstructed drainage lumens of drainage tubes without resorting to manual stripping techniques and which is highly effective.

It is a still further object of the present invention to provide an adaptable multi-lumen drainage tube that may be introduced surgically in the conventional manner and selectively and securely coupled with separate drainage tube adaptors for effecting simple, single lumen drainage and more complex, multi-lumen drainage augmented by irrigation and/or ventilation capabilities.

It is another object of the present invention to provide a drainage lumen clean-out apparatus and method that is simple to use and does not require retraction of the tube.

In accordance with one aspect of the present invention, a wound drainage system is provided which includes an elongated catheter or tube having at least two lumens extending between proximal and distal ends thereof, the lumens terminating in one or more openings at or near the distal end of the tube, wherein the drainage lumen is provided with an opening at the proximal end of the tube and the additional, auxiliary lumen or lumens are obstructed at the proximal end thereof, and wherein the system further includes a set of adaptors for adapting the tube to single lumen and multi-lumen uses. In this aspect of the invention, each adaptor in the set includes a main drainage lumen with a first drainage lumen connector for connecting with the proximal opening of the drainage lumen and a second drainage lumen connector for making connection with a suitable collection vessel and suction apparatus for applying a suction pressure through the adaptor and to the drainage lumen, and wherein the multi-lumen adaptors further include at least one secondary lumen and lumen connector for making connection with the auxiliary lumen when the obstruction in the proximal end thereof is opened and having a connector adapted to be coupled to secondary drainage facilitating structures, such as anti-bacterial air filters for ventilation or a source of irrigation fluid or the like.

In accordance with the first aspect of the invention, the multi-lumen drainage tube or catheter body includes the primary drainage lumen and separate auxiliary lumen or lumens that are supplied with obstructed proximal ends wherein the tube may be used a simple, single lumen drainage tube, or as a multi-lumen drainage tube by removal of the obstruction(s) from the proximal end(s) of the auxiliary lumen(s) and connection of the proximal end of the drainage tube to the corresponding single or multi-lumen adaptor. Preferably, the drainage tube or catheter body is provided with an integral mechanism for aiding in its surgical placement and attachment to the selected adaptor.

In the second aspect of the invention, which may employ the adaptable multi-lumen drainage tube of the first aspect of the invention or prior art drainage tubes, the adaptors used therewith are provided with a clean-out mechanism for the drainage lumen that includes a flexible, elongated clean-out catheter that may be selectively inserted into and advanced down the length within the main drainage lumen to the distal end of the catheter to penetrate through and detach accumulated matter which is attached at its proximal end to a high suction pressure pump for evacuating the loosened obstructing matter from the main drainage lumen through the clean-out catheter lumen. In accordance with the second aspect of the present invention, the clean-out catheter preferably is provided with one or more side openings at the distal end thereof and an opaque radiographic marker which, under appropriate circumstances, may be radiographically imaged under fluoroscopy to observe the progress of the clean-out catheter through the main drainage lumen.

Furthermore, in accordance with the second aspect of the invention, the adaptor through which the clean-out catheter is introduced preferably includes a main lumen connector adapted to be connected to the drainage lumen and having two branches extending therefrom. The main branch preferably includes a valve for closing the first branch and a further connector for connection of the main drain lumen to the fluid collection vessel and low pressure pump when the valve is opened. The second branch preferably includes a connector having a fluid seal therein that bears against the exterior surface of the clean-out catheter and through which the clean-out catheter may be advanced and retracted. The clean-out catheter is preferably encased within a flexible, compressible sheath wherein both the sheath and the proximal end of the clean-out catheter are joined at a normally-closed valve and connector body adapted to be connected to a high suction pressure source and collection vessel.

In accordance with the method of using the lumen clean-out apparatus of the second aspect of the invention, the valve in the first branch of the adaptor is normally opened to apply low pressure suction to the main drain lumen while the valve between the proximal end of the clean-out catheter and the high suction pressure source is normally closed. When it is necessary to clean-out the main drain lumen, the valve in the main first branch of the adaptor is closed and the clean-out catheter is manually advanced through the second branch and down the main drain lumen until an obstruction is detected or the distal end of the clean-out catheter is fully advanced. In either case, the high suction pressure valve is opened for a short period of time to aspirate the obstructing matter through the lumen of the clean-out catheter and collect it in an appropriate collection vessel. Thereafter, the clean-out catheter is withdrawn so that its distal end resides in the second branch of the adaptor and the high suction pressure valve is released to its normally closed position. In this process, the exterior surface of the clean-out catheter remains enclosed within the sterile confines of the flexible, collapsible sheath which surrounds it.

In accordance with further embodiments of the second aspect of the invention, the adaptor and clean-out assembly may be provided with further parallel tubular lumens, valves and anti-bacterial air filters to provide a set of adaptors which may be used with multi-lumen catheters to effect ventilation and/or irrigation of the body cavity.

BRIEF DESCRIPTION OF THE DRAWINGS

These and other objects, advantages and features of the present invention will become apparent from the following detailed description of the preferred embodiments thereof taken in conjunction with the drawings in which like structures and features of the various embodiments are denoted by the same identifying numbers, and in which:

FIG. 5 is a perspective view of the assembly of FIG. 4 with the clean-out tube advanced.

The drawings are not necessarily to scale.

DETAILED DESCRIPTION OF THE PREFERRED EMBODIMENTS

Figure 1:
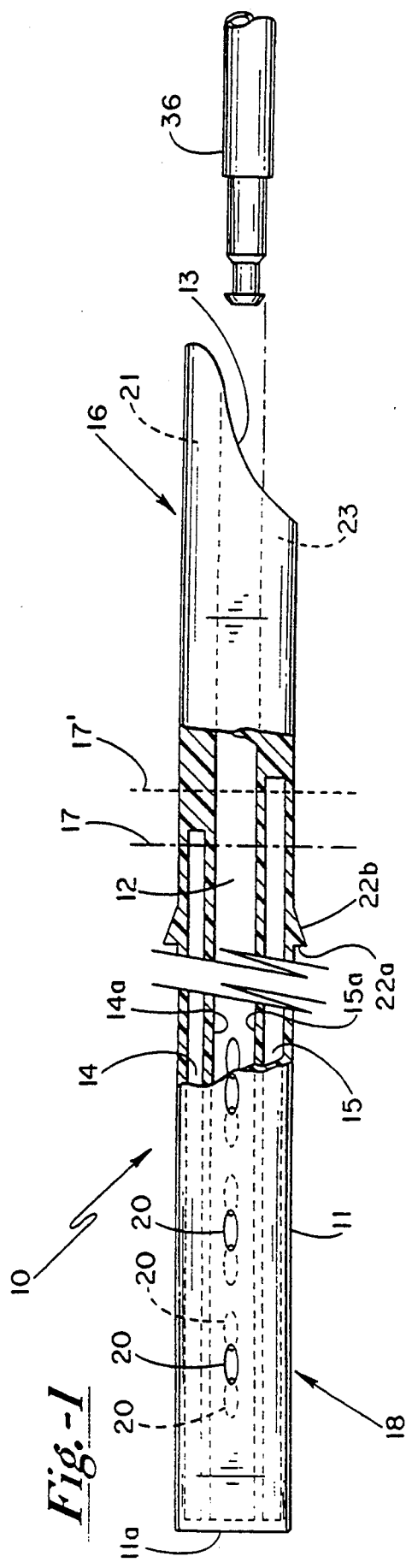
FIG. 1 is a side elevation view of an adaptable, multi-lumen drainage tube in accordance with the invention.

FIG. 1 is a perspective view of a drainage tube 10 constructed in accordance with the first aspect of the present invention wherein it may be employed as either a single or a multi-lumen drainage tube or suction catheter. The drainage tube 10 is configured as a catheter body 11 with a main, large diameter, drainage lumen 12 and auxiliary, smaller diameter, lumens 14 and 15, which are formed within and extend from the proximal end 16 to the distal end 18 of the catheter body 11. Fluid drainage inlets 20 are placed along the length of the drainage lumen 12 near the distal end 18 of the drainage tube 10 and extend through the opposite sides of the catheter body 11. The elongated proximal end 16 of the body 11 is cut on the bias as shown so that it is easier to tunnel it subcutaneously from the site to be drained to an exit point through the skin as described above.

The auxiliary or secondary smaller diameter lumens 14 and 15 extending along side the main, large diameter, drainage lumen 12 are unobstructed from their distal openings in the distal end 18 of the tube 10 to a point near the proximal end 16 thereof. At the proximal end 16, the lumens 14 and 15 are obstructed by molded in place plugs 21 and 23, respectively. Preferably the lumens 14, 15 are formed within the catheter body 11 by webs 14a, 15a, respectively, extending between the sidewalls of the body 11, although they may be formed in other known configurations.

The body 11 of the multi-lumen drainage tube 10 may be molded or drawn from typically used materials, e.g. polyvinyl chloride, polyurethane or silicone rubber compounds. The obstructions 21, 23 in the proximal openings of the auxiliary lumens may be integrally molded in during the fabrication process or be separately fabricated as plugs and inserted into the proximal portions of the lumens 14, 15.

After the proximal end 16 of the tube 10 is exposed through the skin excision, the proximal opening 13 of the drainage lumen 12 is adapted to be coupled through an adaptor to a vacuum source and fluid collection vessel system of the type described, for example, in the above-referenced U.S. Pat. No. '606 patent, incorporated herein by reference in its entirety. The coupling with such an adaptor may be made at the tapered proximal end 16 as shown or to a squared end created by cutting through the catheter body in the proximal end 16 region where the lumens 14 and 15 are obstructed by the molded in place plugs 21 and 23.

Preferably, the proximal end of the multi-lumen tube 10 is also formed with an annular ring 22 molded to it distally from the proximal end 16 and the cutting lines 17. The distance also should be sufficiently long that the portion of the tube 10 remaining after severance at cutting line 17 may be connected to the selected adaptor. The annular ring 22 is wedge shaped in profile so that its annular distal flange 22a provides an attachment surface with an attachment mechanism of the adaptor in a manner to be described. The conical surface 22b of the annular ring 22 facilitates advancing the proximal end 16 subcutaneously and also provides an attachment surface onto which the adaptor lumen may be press fit in a manner to be described.

Figure 2:
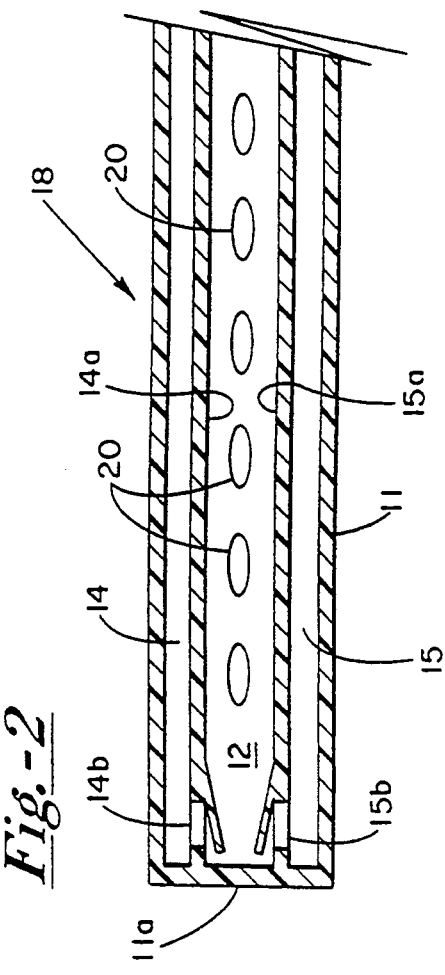
FIG. 2 is a detail view of the construction of the distal end of the drainage tube of FIG. 1.

The distal end 18 of the drainage tube 10 is shown in greater detail in FIG. 2. The distal ends of the lumens 12, 14, 15 are blocked by a distal end wall 11a for reasons to be described in reference to further preferred embodiments of the invention. In regard to this aspect of the invention, the distal end of the lumen 12 may be left open so that drainage may take place through the open end as well as the sidewall inlets 20. In either case, it is contemplated that the distal ends of the auxiliary lumens 14 and 15 may be provided with flap valves or slits in the webs 14a and 15a in the areas designated 14b and 15b, respectively, so that body fluid would be inhibited from entering lumens 14 and 15 if either or both auxiliary lumen is left plugged at the proximal ends thereof and unused. If either or both are used to irrigate and/or introduce filtered air, the introduced fluid or air would be drawn through the valves at 14b and/or 15b by the suction applied through the main lumen 12.

In accordance with the first aspect and preferred embodiments of the present invention, it is contemplated the proximal end 16 of the multi-lumen catheter 10 may be coupled to a selection of adaptors having a one, two or three tubular connectors, lumens and valves and the like for configuring the drainage tube 10 as a single lumen or multi-lumen drainage system with appropriate external equipment. In FIG. 1, a simple tubular connector 36 is shown for direct insertion into opening 13 of lumen 12 to illustrate the use of the drainage tube 10 as a simple, single lumen drainage catheter with or without cutting off the tapered portion of the proximal end 16.

In accordance with the first aspect of the invention, it is contemplated that the surgeon may select the appropriate adaptor and, if a multi-lumen drainage system is chosen, the proximal end 16 may be partially or completely severed along the dotted line 17 to cut across and open one or both of the lumens 14, 15 thereby removing one or both of the obstructions 21, 23. The actual point of severance of the dotted line 17 preferably is at a distance from the annular ring 22 that allows it to cooperate with attachment structure of the adaptor in a manner to be described. In this fashion, only one, multi-lumen, drainage tube 10 need be stocked for multiple usages with the appropriate adaptors, many of which are already available for use with the appropriate selected single or multi-lumen drainage tube.

Figure 3:
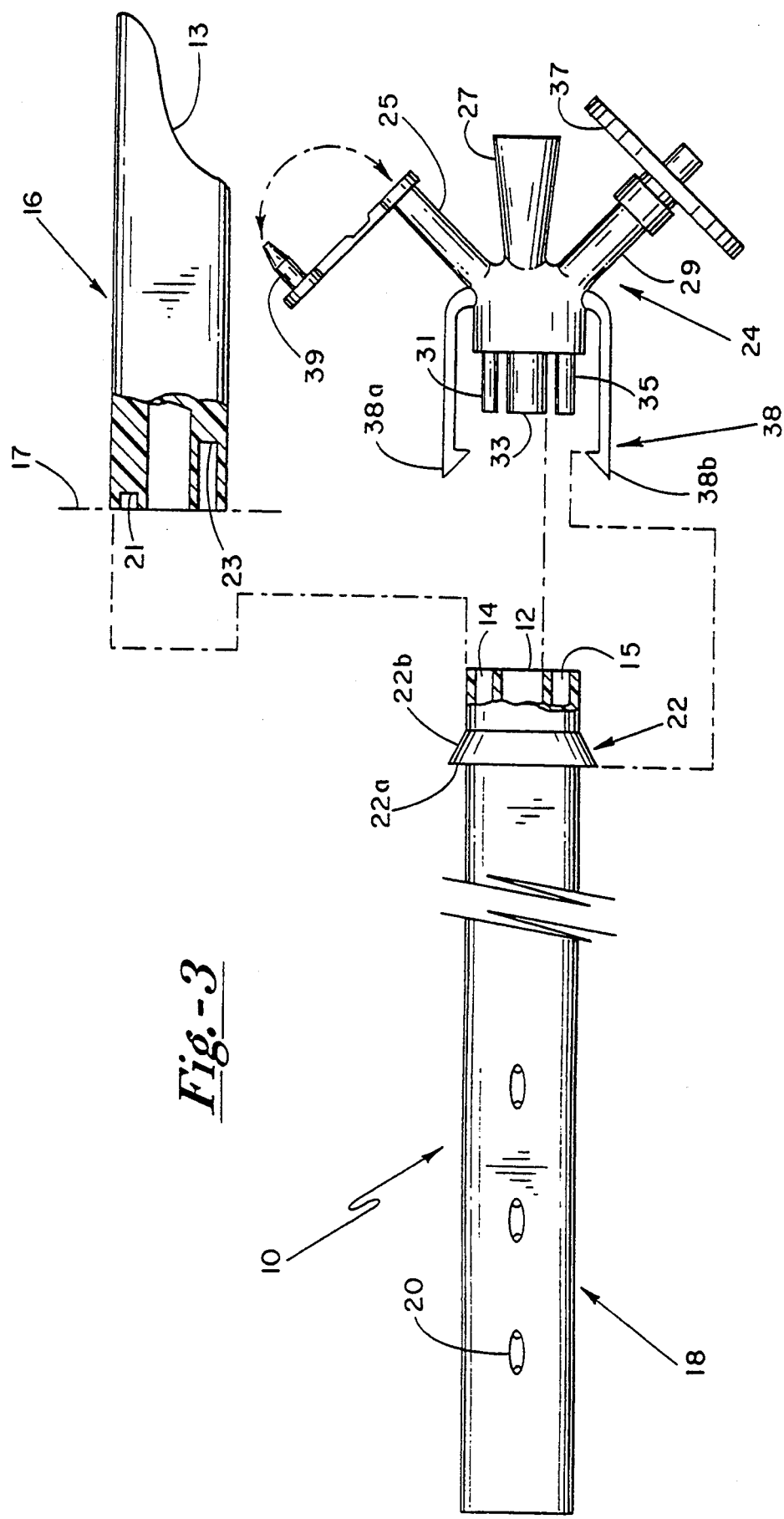
FIG. 3 is an illustration of the modification of the catheter of FIG. 1 to couple it with a suitable configured multi-lumen adaptor in accordance with the first aspect of the invention.

FIG. 3 illustrates the severing of the proximal end 16 of the body 11 of the drainage tube 10 along the line 17 and the fitting of a drainage, ventilation and irrigation adaptor 24 thereto. Adaptor 24 has three tubular adaptor branches 25, 27 and 29 each enclosing separate lumens and which extend between three respective adaptor connectors 31, 33, and 35 that are adapted to be inserted into the exposed lumens 14, 12 and 15 which are exposed by severing the proximal end 16 of the drainage tube 10 along the line 17. The tubular adaptor branch 25 includes an integrally attached and formed stopper 39. The lumen of adaptor branch 25 may be connected to a source of irrigating fluid in a manner known in the art. The tubular adaptor branch 27 is adapted to be coupled to the fluid collection vessel and low suction pressure source incorporated herein by reference. The tubular adaptor branch 29 is adapted to be connected to an anti-bacterial filter assembly 37 of a type well known in the art for preventing airborne infection of the wound which is being drained. Optionally, one or more of the tubular adaptor branches 25, 27, 29 may include a stop-cock valve, and the adaptor branch 27 may include a reverse flow prevention reed valve, of types known in the art, if desired.

The adaptor 24 is preferably fabricated of a relatively hard plastic material in comparison to the softer and more flexible material of the drainage tube 10. The adaptor branches 25, 27, 29 are formed with respective adaptor connectors 31, 33, 35. The attachment of the adaptor connectors 31, 33, 35 to the drainage tube 10 lumens 14, 12, 15, respectively, may be facilitated by a flexible locking mechanism 38 having two or more hooks 38a, 38b which is attached to the adaptor 24. In use, the relatively stiff adaptor tubes are manually inserted into the lumens 14, 12, 15, respectively, and the hooking members 38a, 38b extend over the annular ring 22 and catch on the flange 22a. Thus the annular ring 22 can be employed both in the surgical procedure and to secure attachment of the adaptor 24 to the tube 10.

The three lumen adaptor 24 as described above is conventional in the prior art except for the attachment mechanism 38. In accordance with the invention, the adaptor 24 (with or without the attachment mechanism 38) may be used with the universal drainage tube of FIGS. 1 and 2 by severing the body 11 at the line 17 and inserting the adaptor connectors 31, 33, 35 into the proximal openings of the drainage tube lumens 14, 12, 15, respectively. Similarly, a two lumen adaptor of conventional design may be attached to a pair of the tube lumens 12 and 14 or 15 by selectively cutting across the body 11 in the proximal end 16 to open the selected auxiliary lumen 14 or 15 while leaving the other auxiliary lumen 15 or 14, respectively, occluded by a short section of the obstruction 23 or 21. To facilitate the selection of the otherwise identical auxiliary tube lumens 14 and 15, one of the obstructions, e.g. 21, may be extended distally more than the other, and the cutting line 17' may be used to open only tube lumen 15. The typically colorless body 11 or the obstructions 21 and 23 of the drainage tube 10 may be marked or color coded to alert the user of the options available and recommended cutting lines for one, two or three lumen usage as described above with the appropriate adaptor. Since the remaining length of the proximal end 16 differs, depending on which cutting line 17 or 17' is chosen, the two two and three lumen adaptors may be provided with attachment mechanisms 38 having hooking members 38a, 38b that are long enough to engage the annular flange 22a in each instance.

Thus, in the first aspect of the present invention, the multi-lumen drainage tube 10 may be universally used in substitution for separate single, double lumen and triple lumen drainage tubes and with the appropriate adaptor to avoid duplicate stocking of the differing drainage tubes. The distal end 18 of the tube 10 may be provided with a radiopaque marker to facilitate its location, as well as the location of the entire tube, if it should become lost subcutaneously.

Figure 4:
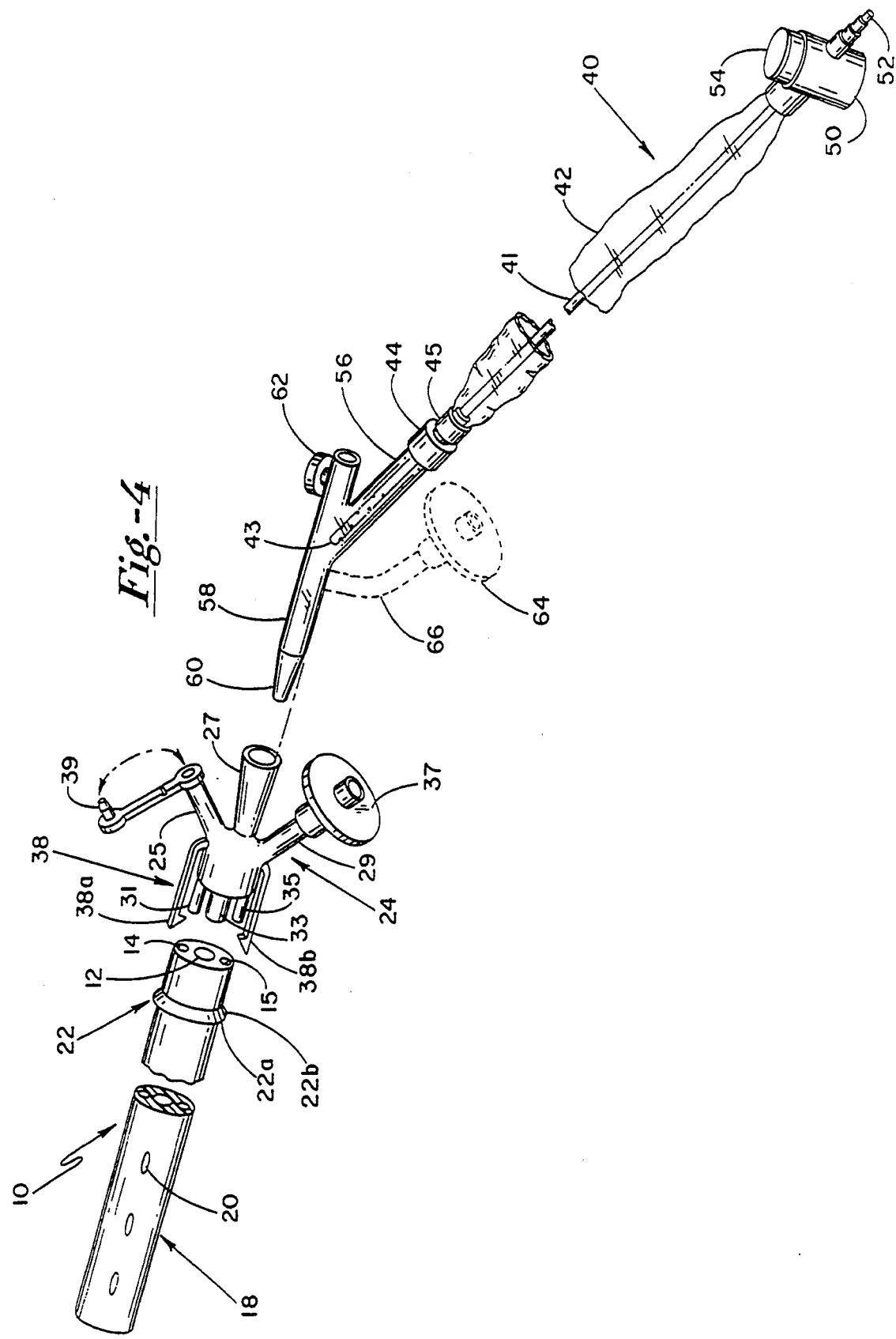
FIG. 4 is a perspective view of a first embodiment of a further adaptor constructed in accordance with the second aspect of the present invention for effecting clean-out of the main drainage lumen of a drainage tube of a type depicted in FIG. 1 wherein the clean-out tube is fully retracted.

Turning now to the second aspect of the present invention illustrated in FIGS. 4 and 5, the adaptors, e.g. adaptor 24, for use with the multi-lumen drainage tubes 10 of FIGS. 1–3 are provided with a clean-out mechanism 40 for dislodging and removing obstructions, e.g. clots and tissue fragments referred to as "obstructing matter" that may build up in the large diameter, main drainage lumen 12 due to the affinity of slow moving blood to clot by itself or around other debris and particularly to foreign body materials, such as the polyvinyl chloride or silicone rubber that the flexible, elongated tube 10 is typically constructed of. This tendency to clot and form obstructing matter in drainage tube lumens is well known and, as described above, is aggravated by the necessity of employing low suction pressures and consequent low drainage rates of flow.

The clean-out apparatus 40 preferably comprises an elongated, thin bodied and relatively small diameter, polyvinyl chloride or silicone rubber clean-out catheter 41 having a distal end 43 extending within a side branch 56 of an elongated, auxiliary clean-out adaptor 58. An adaptor fitting 60 of the adaptor 58 is press fit into the opening of the center branch 27 lumen of the adaptor 24 and the other end of auxiliary adaptor 27 is coupled to a stop-cock valve 62 which in turn is adapted to be coupled to the suction and drainage apparatus.

In FIG. 4, the clean-out catheter 41 is illustrated in its normal, retracted position, wherein a thin, plastic sheath 42 loosely envelops the catheter 41 in a manner shown in U.S. Pat. No. 5,073,164 to Hollister et al., incorporated herein by reference in its entirety. The length of the catheter 41, when fully extended distally, is selected to extend distally down the main lumen 12 to the distal end 18 of the drainage tube or catheter 10 as shown in FIG. 5. In addition, the diameter of the catheter 41 is selected so that it does not easily pass through the distal fluid drainage inlets 20.

The sheath 42 is attached to a fitting 44 which in turn is attached to the free end of the side branch 56 and contains a wiper seal 45 of the type disclosed in the U.S. Pat. No. '164 patent and referred to as "wiper seal 5." The other end of the sheath 42 and the end of the clean-out catheter 41 are fixedly attached to a normally-closed valve 50 which corresponds to the "suction valve assembly 1" of the above incorporated U.S. Pat. No. '164 patent. The environmentally sealed attachment of the sheath 42 to the fitting 44 and the normally-closed valve 50 ensures that the catheter 41 remains sterile but may be advanced from its normal retracted position depicted in FIG. 4 into an advanced position depicted in FIG. 5 whereby its distal end 43 is advanced down the lumen 12 to the distal end 18 of the multi-lumen drainage tube 10 to effect a clean-out thereof.

In normal use, the catheter 41 is retracted so that its distal end 43 is in the lumen of side branch 56 as shown in FIG. 4. The clean-out procedure involves the closure of a stop-cock valve 62 to close off the main branch lumen 27 and attachment of a conventional high suction fluid drainage collector (not shown) to the nozzle shaped fitting 52 proximal to the valve 50. The valve 50 is opened by depressing button 54 as the catheter 41 is advanced distally through the wiper seal 45, the adaptors 58 and 24, and down the lumen 12. In the clean-out procedure, higher than normal suction pressures could be repetitively applied by briefly opening valve 50. During advancement of the catheter 41, the sheath 42 collapses upon itself in an accordion-like manner to accommodate the movement of the internally disposed catheter 41 with respect thereto. In multi-lumen catheter embodiments including an irrigation lumen (as shown in FIGS. 4 and 5), irrigating fluid may be introduced through the lumen in adaptor branch 25 while the catheter 41 is advanced distally so as to increase the fluid outflow to sweep away dislodged obstructions.

Thus, in use, medical personnel may initiate the clean-out of the drainage tube periodically or on an as-needed basis simply by attaching the fitting 52 to a high vacuum fluid collection system and manually advancing the catheter 41 down the lumen 12 while continuously or periodically opening and closing the valve 50 to remove blood clots or other body tissue dislodged in the advancement of the distal end of the catheter. The stopcock valve 62 is closed during the clean-out procedure. After fully advancing the clean-out catheter 41 and observing the passage of such matter through the transparent catheter body, the catheter 41 is withdrawn back to its retracted position and stop-cock valve 62 opened so that the resulting flow through the lumen of the main branch 27 lumen of the adaptor 25 may be observed to ensure that the clean-out procedure was effective.

The auxiliary clean-out adaptor 58 is shown in FIGS. 4 and 5 as separate from the adaptor 24. The separate clean-out adaptor allows its use with the unsevered, single lumen catheter shown in FIG. 1 or with any conventional single lumen drainage tube or conventional two or three lumen drainage tubes with appropriate adaptors. In use with a single lumen drainage tube, the clean-out adaptor 58 preferably includes an antibacterial air filter assembly 64 and auxiliary branch 66 (depicted in dotted lines in FIG. 4). All other elements of the embodiment operate in the same manner as described in respect to the preceding embodiment.

It will also be understood that the clean-out adaptor 58 and assembly 40 may be made as a unitary structure with the three lumen adaptor 24 illustrated as well as the two lumen adaptor for use with the universal catheter of FIG. 1 or with conventional multi-lumen drainage tubes.

It will thus be appreciated that the clean-out apparatus 40 of the second aspect of the invention relating to the removal of obstructing matter from the drainage lumen of a drainage tube may be employed with single lumen, dual lumen or triple lumen drainage tubes known in the prior art. Moreover, it may be used with respect to other drainage or infusion catheters employed for other medical purposes.

The invention has been described in respect to the preferred embodiments and the several aspects thereof. It will be appreciated that various changes, modifications and substitutions of equivalent elements of the structures and methods of the preferred embodiments can be made without departing from the spirit and scope of the present invention.

What is claimed is:

1. An adaptable surgical drain for use with external drainage facilitating equipment in evacuating body fluids accumulating inside the body percutaneously into fluid vessels comprising:

a multi-lumen catheter body having proximal and distal ends, including a drainage lumen extending between openings in the proximal and distal ends thereof and at least one auxiliary lumen extending between openings in the proximal and distal ends thereof; and a molded in place obstruction obstructing the proximal end opening of at least one auxiliary lumen, whereby, in use, the obstruction may be left intact in order to use the multi-lumen catheter body as a single lumen surgical drain or the obstruction may be severed and the catheter body used as a multi-lumen surgical drain.

2. The surgical drain of claim 1 wherein the catheter body further comprises: first and second auxiliary lumens extending between respective openings in the proximal and distal ends thereof; and molded in place obstructions obstructing the proximal end openings of the first and second auxiliary lumens that are selectively removable to use the surgical drain with irrigation and ventilation.

3. The surgical drain of claim 2 wherein the catheter body is constructed of a soft, pliant material capable of being severed in the proximal end region to cut away the obstructions in the proximal end openings of one or both of the auxiliary lumens thereof.

4. The surgical drain of claim 3 wherein the multi-lumen catheter body is constructed of a material selected from the group comprising polyvinyl chloride and silicone rubber compounds.

5. The surgical drain of claim 1 wherein the catheter body is constructed of a soft, pliant material capable of being severed in the proximal end region to cut away the obstruction in the proximal end opening of the auxiliary lumen thereof.

6. The surgical drain of claim 5 wherein the multi-lumen catheter body is constructed of a material selected from the group comprising polyvinyl chloride and silicone rubber compounds.

7. A surgical wound drainage assembly for use with external drainage facilitating equipment in evacuating body fluids accumulating inside the body percutaneously into fluid vessels comprising:

a multi-lumen catheter body having a drainage lumen extending between proximal and distal end openings in the proximal and distal end of the catheter body and at least one auxiliary lumen extending in parallel with the main lumen between proximal and distal openings in the proximal and distal ends of the catheter body;

a molded in place obstruction obstructing the proximal opening of at least one auxiliary lumen;

first adaptor means for selective attachment with only the proximal opening of the drainage lumen for coupling the drainage lumen with the external drainage facilitating equipment and leaving the proximal opening of the auxiliary lumen obstructed; and second adaptor means for alternative selective attachment with both the proximal opening of the drainage lumen and the unobstructed opening of the auxiliary lumen, wherein the obstruction in the auxiliary lumen is severed to effect connection with the second adaptor means.

8. The assembly of claim 7 wherein the catheter body further comprises:

first and second auxiliary lumens extending between respective openings in the proximal and distal ends thereof; and molded in place obstructions obstructing the proximal end openings of the first and second auxiliary lumens that are selectively removable to use the surgical drain with irrigation and ventilation.

9. The assembly of claim 8 wherein the catheter body further comprises third adaptor means for alternative selective attachment with both the proximal opening of the drainage lumen and the unobstructed openings of the first and second auxiliary lumens, wherein the obstructions in the auxiliary lumens are severed to effect connection with the third adaptor means.

10. The assembly of claim 9 further comprising:

means adapted to be coupled to each of the adaptor means for applying suction pressure through each of the adaptor means and the drainage lumen attached thereto for suctioning out and collecting body fluids from a patient's body.

11. The assembly of claim 8 further comprising:

suction and collection means adapted to be coupled to the adaptor means for applying suction pressure through the adaptor means and the drainage lumen attached thereto for suctioning out and collecting body fluids from a patient's body; and wherein the adaptor means further comprises:

an adaptor body adapted to be coupled to the proximal end opening of the drainage lumen and having a main lumen extending therethrough to a fitting for attachment to the suction and collection means and having a side branch extending from the main lumen to a further fitting for providing access through a lumen in the side branch to the lumen in the adaptor and the drainage lumen; and means attached to the fitting in the side branch of the adaptor body adapted to be advanced into the main lumen and the fluid drainage lumen for periodically effecting the removal of obstructions accumulating within the drainage lumen.

* * * * *